(12) United States Patent
Shames et al.

(10) Patent No.: US 10,159,413 B2
(45) Date of Patent: Dec. 25, 2018

(54) APPARATUS AND METHOD FOR NON-INVASIVE MEASUREMENT OF BLOOD PARAMETERS

(71) Applicant: ANATECH ADVANCED NMR ALGORITHMS TECHNOLOGIES LTD., Nirit (IL)

(72) Inventors: Alexander Shames, Beer-Sheva (IL); Yuri Rozenfeld, Yeruham (IL); David Keini, Haifa (IL)

(73) Assignee: ANATECH ADVANCED NMR ALGORITHMS TECHNOLOGIES LTD., Nirit (IL)

( * ) Notice: Subject to any disclaimer, the term of this patent is extended or adjusted under 35 U.S.C. 154(b) by 766 days.

(21) Appl. No.: 14/377,335

(22) PCT Filed: Feb. 5, 2013

(86) PCT No.: PCT/IL2013/050104
§ 371 (c)(1),
(2) Date: Aug. 7, 2014

(87) PCT Pub. No.: WO2013/118115
PCT Pub. Date: Aug. 15, 2013

(65) Prior Publication Data
US 2015/0018638 A1 Jan. 15, 2015

Related U.S. Application Data
(60) Provisional application No. 61/596,569, filed on Feb. 8, 2012.

(51) Int. Cl.
*A61B 5/0205* (2006.01)
*G01R 33/44* (2006.01)
(Continued)

(52) U.S. Cl.
CPC ...... *A61B 5/02055* (2013.01); *A61B 5/02035* (2013.01); *A61B 5/055* (2013.01);
(Continued)

(58) Field of Classification Search
CPC ... A61B 5/055; A61B 5/14532; A61B 5/6826; A61B 5/14539; A61B 5/02035;
(Continued)

(56) References Cited

U.S. PATENT DOCUMENTS 4,875,486 A    10/1989   Rapoport et al.
5,072,732 A *   12/1991   Rapoport ............... A61B 5/055
                                               324/308

(Continued)

FOREIGN PATENT DOCUMENTS

DE       2035858 A1    1/1972
EP       0621491 A2    10/1994
(Continued)

OTHER PUBLICATIONS

Graaf et al., In Vivo Glucose Detection by Homonuclear Spectral Editing, Magnetic Resonance in Medicine 43:621-626, 2000.*
(Continued)

*Primary Examiner* — Bo Joseph Peng
(74) *Attorney, Agent, or Firm* — Browdy and Neimark, PLLC

(57) ABSTRACT

The present invention provides techniques for non-invasive measurement of blood related parameters based on NMR (nuclei) relaxation techniques carried out using a relatively low constant magnetic field in the range of 0.15 to 0.5 Tesla. A plurality of electromagnetic excitation pulse sequences having relatively low radiofrequencies are applied over a living tissue placed in the magnetic field and blood related parameters of the examined subject are determined using a plurality of nuclear spin echo signals received from the (Continued)

tissue in response to the applied excitation sequences, thereby allowing to improve the accuracy of the obtained signals and substantially reducing the time duration of the process.

14 Claims, 4 Drawing Sheets

(51) Int. Cl.
    *A61B 5/055*     (2006.01)
    *A61B 5/145*     (2006.01)
    *A61B 5/02*     (2006.01)
    *A61B 5/00*     (2006.01)
    *G01R 33/383*     (2006.01)
    *G01R 33/46*     (2006.01)

(52) U.S. Cl.
    CPC ...... *A61B 5/14532* (2013.01); *A61B 5/14535* (2013.01); *A61B 5/14539* (2013.01); *A61B 5/14542* (2013.01); *A61B 5/6826* (2013.01); *G01R 33/448* (2013.01); *G01R 33/383* (2013.01); *G01R 33/4608* (2013.01)

(58) Field of Classification Search
    CPC ............ A61B 5/14542; A61B 5/02055; A61B 5/14535; G01R 33/383; G01R 33/4608; G01R 33/448
    See application file for complete search history.

(56) References Cited

U.S. PATENT DOCUMENTS

| | | | |
|---|---|---|---|
| 5,320,103 A * | 6/1994 | Rapoport | G01R 33/383 324/318 |
| 5,592,086 A | 1/1997 | Weinstock et al. | |
| 5,685,300 A | 11/1997 | Kuenstner | |
| 6,163,154 A | 12/2000 | Anderson et al. | |
| 6,404,197 B1 | 6/2002 | Anderson et al. | |
| 7,635,331 B2 | 12/2009 | Kim et al. | |
| 7,695,953 B2 | 4/2010 | Gould et al. | |
| 7,940,045 B2 | 5/2011 | Carpenter et al. | |
| 2006/0097722 A1* | 5/2006 | Scheven | G01V 3/32 324/303 |
| 2007/0035296 A1 | 2/2007 | Potapov et al. | |
| 2007/0116602 A1 | 5/2007 | Lee | |
| 2007/0178598 A1 | 8/2007 | Jeyarajah et al. | |
| 2009/0203345 A1* | 8/2009 | Sorrells | H03C 1/62 455/313 |
| 2010/0030062 A1 | 2/2010 | Bolar et al. | |
| 2011/0109310 A1 | 5/2011 | Hornung | |
| 2011/0128000 A1 | 6/2011 | Harvey | |
| 2012/0197107 A1 | 8/2012 | Griswold | |
| 2014/0194715 A1 | 7/2014 | Griswold | |

FOREIGN PATENT DOCUMENTS

| | | |
|---|---|---|
| EP | 2292142 A1 | 3/2011 |
| RU | 2003121084 A | 1/2005 |
| WO | 9216851 A1 | 10/1992 |
| WO | 2012118442 A1 | 9/2012 |

OTHER PUBLICATIONS

Silvennoinen "A Study of NMR Relaxation in Blood-Mechanistic Considerations and Implications for Quantitative Functional MRI". PhD diss. University of Kuopio, Finland. XP055197360. 1-62 (2002).
Wright et al. "Estimating Oxygen Saturation of Blood in Vivo with MR Imaging at 1.5 T", Journal of Magnetic Resonance Imaging, 1(3): 275-283. XP055197353 (1991).
European search report, dated Jun. 23, 2015, in corresponding application No. EP13746441.
Protasov, E. A., et al. "Determination of glucose content in human blood by NMR method," Scientific session MEPhI Conference, 5: 3. (2003).
Bonny, J.M., et al. "Multi-exponential analysis if magnitude MR images using a quantitative multispectral edge-preserving filter", Journal of Magnetic Resonance, 161:1: 25-34. (Mar. 2003).
Brooks, R. A., et al. "Nuclear Magnetic Relaxation in Blood", IEEE Transactions on Biomedical Engineering, 22:1: 12-18. (Jan. 1975).
International search report dated May 28, 2013. In corresponding application No. 2013050104.

* cited by examiner

APPARATUS AND METHOD FOR NON-INVASIVE MEASUREMENT OF BLOOD PARAMETERS

TECHNOLOGICAL FIELD

The present invention is generally in the field of medical applications and relates to an apparatus and method for non-invasive in vivo assessment of blood parameters, such as, for example, blood glucose content, blood viscosity, haematocrit, oxygen saturation and pH, using pulsed nuclear magnetic resonance (NMR) relaxometry techniques.

BACKGROUND

There is an ongoing effort to develop non-invasive techniques for determining body fluid constituents, such as parameters of living blood. These non-invasive measurement techniques aim to simplify the test and constituents determination procedures, and substantially alleviate the discomfort associated with conventional invasive tests commonly used nowadays.

In case of diabetes, for example, diabetic patients must measure blood glucose by themselves on a daily basis by an ex vivo blood test. Self-monitoring of blood glucose is an important component of modern therapy for diabetic patients and offers information about blood glucose levels, and in many time points to enable stabilization of glucose levels in everyday life. The self-monitoring of blood glucose is suggested to be undertaken at least three or four times a day. However, it is reported that only 18% of diabetic patients periodically measure blood glucose levels, even in good social welfare sectors such as in the USA. Blood glucose measurement negligence is mainly due to invasive-type glucose meters that are used nowadays, that require in each test that blood samples be directly taken from the body of the patient e.g., by piercing a finger of the patient. Such periodical blood tests employing the invasive method not only cause pain and discomfort during the blood taking process, but also impose mental and economic burdens with considerable costs of consumable accessories necessary for the blood taking operation.

Various devices for non-invasive measurement of blood glucose have been developed aiming to prevent the pain and displeasure associated with the conventional blood taking process, to reduce use of diagnostic strips and the costs associated therewith, and to allow smoothly performing self-measurement of blood glucose levels. Such non-invasive blood glucose measurement techniques include, for example, analysis of a absorption spectrum in an infrared zone, impedance spectroscopy in a band of tens to hundreds MHz, and non-invasive blood glucose measurement based on NMR spectroscopy.

Some NMR based blood test techniques known from the patent literature will be briefly discussed below.

U.S. Pat. Nos. 4,875,486, 5,685,300, 6,163,154, 6,404,197 and US patent publication No. 2010/030062A1, disclose NMR based techniques that are basically based on correlation between resonance peaks (or areas) appearing in NMR spectrum of blood (or of tissue) of the human body due to water and glucose components, or on a degree of chemical shift by the glucose component on the measured NMR caused by variations in a blood glucose concentration.

In the publication by Protasov et al., (E. A. Protasov, O. C. Esikov and E. C. Karpova, "*Measurement of concentration of glucose in human blood by NMR method*," Scientific session MEPhI Conference, Vol. 5, pp. 3, 2003) a glucose concentration measurement method is described wherein an electromagnetic field is used and blood glucose levels are determined based on correlation between blood glucose levels measured in healthy subjects and a NMR spin-lattice relaxation time measured by a NMR absorption method.

U.S. Pat. No. 7,635,331 discloses a blood glucose sensor using permanent magnets to non-invasively measure blood glucose by means of the NMR absorption method applied to a human finger. In this non-invasive blood glucose sensor, a pair of permanent magnets is used to apply a constant magnetic field so as to remove variations in the magnetic field caused by an unstable power supply. A triangular waveform low frequency modulation magnetic field having uniform strength is used together with a weak acoustic wave modulation magnetic field to determine nuclear spin-lattice relaxation time of the finger's protons from changes of the NMR absorption signal as a function of low frequency modulation sequence. Blood glucose concentration is then determined by correlating between pre-determined blood glucose levels in healthy subjects and the determined proton spin-lattice relaxation time.

International patent publication No. WO 2012/118442 discloses techniques for ex vivo determining infection level of blood cells using magnetic resonance relaxometry. In this publication, a magnetic resonance relaxometry system is used to examine a sample of concentrated red blood cells taken from an examined subject by placing the red blood cells sample within a detection coil of the apparatus and determining an infection level based on transverse relaxation rates.

A non invasive blood fluidity measurement technique is described in EP 2,292,142, which suggests measuring the passage of light in a test site in a finger area of a patient, where pressure is applied over the test site in order to squeeze and flow out blood therefrom to the periphery of the test site.

GENERAL DESCRIPTION

There is need in the art for a novel measurement technique for in vivo non invasive measuring various blood related parameters which would provide accurate measurements within a short measurement time (no more than a few minutes) and moreover enable a measurement device to be miniature/portable, e.g., of a hand held configuration.

The inventors of the present invention have surprisingly found that blood parameters of a subject may be non-invasively determined with improved accuracy, and within a relatively short time duration of measurement session, when employing magnetic resonance relaxometry techniques utilizing proper parameters of the magnetic field excitation stage. The apparatus of the present invention operates with a constant magnetic field which is a relatively low field, i.e., in the range of 0.15 to 0.5 Tesla, and electromagnetic excitation signals of relatively low radiofrequencies, i.e., in the range of 1 to 20 MHz. These parameters of the excitation stage enable use of smaller and simpler magnetic elements, thus significantly reducing the size, weight, and complexity of mechanical and electronic circuits of the measurement apparatus.

Decrease in the above parameters of the excitation stage might result in reduction of the signal-to-noise ratio of the detection stage. The present invention solves this problem by providing a certain time pattern for the excitation session and detection session based on relaxation curves associated with blood constituents.

The present invention thus provides a method and apparatus for in vivo non-invasive measurement of blood parameters based on NMR (nuclei) relaxation techniques carried out on an organ (body part of the examined subject, such as a finger phalange, also referred to as a tissue or test organ) over which a relatively low constant magnetic field in the range of 0.15 to 0.5 Tesla is applied. Blood parameters of the examined subject are determined using nuclear spin echo signals received from the test organ in response to specific (e.g., short hard off-resonance) electromagnetic pulse sequences having relatively low radiofrequencies (RF). As will be understood from the following disclosure the techniques described herein allow determining nuclear spin echo signals received from living body tissue and/or fluids of an examined subject in response to electromagnetic excitation signals, with improved selectivity with regard to different blood/tissue components and within relatively short durations of time (e.g., within 1 to 5 minutes).

In general, techniques of the present invention employ a pulsed NMR apparatus to acquire nuclear spin echo signals. The NMR apparatus comprises a probehead configured and operable to accommodate the test organ of the examined subject in a test volume defined thereinside. The probehead is configured and operable to apply the constant magnetic field inside the test volume, apply electromagnetic excitation signals over the test organ located inside the test volume, and acquire electromagnetic signals from the test organ responsive to the applied excitation signals. The excitation signals are applied in some embodiments in a direction substantially perpendicular to the direction of the constant magnetic field.

The NMR apparatus further comprises a receiver configured and operable to process the electromagnetic signals received by the probehead and extract therefrom nuclear spin echo signals. In some possible embodiments the receiver is a single channel receiver. For example, the receiver may comprise a single channel IF receiver configured and operable to down convert the electromagnetic signals received by the probehead from the test organ. The receiver may further comprise a demodulator configured and operable to extract the nuclear spin echo signals from the signals received from the probehead unit. The nuclear spin echo signals are then processed by a processor to determine one or more blood parameters of the tested subject.

The probehead may include a magnetostatic field applying unit comprising a permanent magnet assembly or Helmholtz coils for applying the constant magnetic field. For example, in some embodiments the constant magnetic field is obtained between magnetic poles of a permanent magnet assembly, thereby defining the test volume between the magnetic poles of the permanent magnet assembly. The test volume may be configured in the form of a gap or, alternatively, an elongated chamber adapted to accommodate a finger of the examined subject, or a portion thereof (e.g., one or more finger phalanges).

The probehead further comprises at least one inductive coil located along a length of the test volume under which the constant magnetic field is applied by the magnetostatic field applying unit. The coil is configured and operable to receive a portion of the test organ within its coil turns, to apply the electromagnetic excitation signals along a length of the test organ portion disposed in it, and acquire electromagnetic signals from the test organ responsive to the applied excitation signals. The coil may thus apply electromagnetic excitation signals in a direction substantially perpendicular to the direction of the constant magnetic field applied inside the test volume.

The blood parameters of the examined subject are determined in some embodiments based on relaxation time/relaxation rates extracted from the decaying/uprising nuclear spin echo signals (nuclear magnetization relaxation curves), said nuclear relaxation times/rates associated with different blood constituents of the examined subject. In some embodiments the relaxation times/rates are determined using a multifunctional analysis technique employing multi-dimensional (e.g., two-dimensional, or three-dimensional) data, acquired as sets of one-dimensional spin echo signals obtained with at least one variable delay time, to thereby achieve sensitive, selective and reliable correlations of the measured relaxation times/rates with predetermined relaxation times/rates associated with blood parameters of healthy and deceased subjects.

In some embodiments the excitation signals comprise a plurality of radiofrequency pulse sequences, each pulse sequence comprising two or more radiofrequency pulses having predetermined time durations and predetermined delay times separating between successive pulses in the pulse sequence. Accordingly, responsive to the plurality of pulse sequences, a plurality of decaying/uprising spin echo signals are obtained, the plurality of decaying spin echoes may be processed to obtain spin echo signals with improved signal to noise ratios. The delay times used to separate between successive pulses on the time axis may vary from one pulse sequence to another. For example, the delay times used in successively applied pulse sequences may be gradually increased (or decreased).

There is thus provided an apparatus for use in non-invasive in vivo assessment of blood related parameters (e.g., blood glucose content, blood viscosity, blood haematocrit, blood oxygen saturation, and blood pH) of an examined subject. According to some embodiments the apparatus comprises a signal generator configured and operable to generate excitation signals (e.g., off-resonance excitation pulses) in a radiofrequency range of 1 to 20 MHz and a probehead unit (e.g., having an electromagnetic shield to substantially attenuate external electromagnetic interferences) defining a test site for a living tissue of the subject being examined and comprising a magnetic field source unit configured and operable to generate a substantially uniform magnetic field of about 0.15 to 0.5 Tesla in a magnetic field region in which the test site is located, to thereby magnetize blood in said living tissue, at least one inductive coil (e.g., having a cylindrical or a saddle shape) placed in the test site so as to be in the magnetic field region and to be exposed to the excitation signals, the inductive coil being configured to surround at least a part of the living tissue when placed in said test site, the at least one inductive coil thereby responding to said magnetic field and said RF excitation signals by generation of electromagnetic excitation signals in a direction substantially perpendicular to a direction of the magnetic field to thereby affect the blood magnetization in the living tissue, and generating an electromagnetic response to nuclear spin echo signals from the living tissue.

The apparatus comprises a receiver unit (e.g., a single channel IF receiver) configured and operable to receive the electromagnetic response of the at least one inductive coil and generate measured data indicative thereof, and a control unit connected to the probehead unit for operating the signal generator and to the receiver to provide predetermined time patterns of the generation of the excitation RF signals and of the receipt of the electromagnetic response, the control unit being configured and operable to process the measured data and extract data indicative of the nuclear spin echo signals from the living tissue, to determine relaxation magnetization curves (e.g., $T_{1i}$ spin-lattice relaxation magnetization curves, $T_{1\rho i}$ spin-lattice relaxation magnetization in rotating frame curves, and/or $T_{2i}$ spin-spin relaxation magnetization decays) of blood constituents associated with the blood related parameters, and determine at least one blood related parameter.

The receiver unit may comprise a demodulator configured and operable for demodulating signals associated with the nuclear spin echo signals from the electromagnetic response. The receiver unit may further comprise a signal amplifier for amplifying the electromagnetic response from the coil.

In some applications the control unit comprises a pulse controller module configured and operable to switch the apparatus operation between its excitation and acquisition cycles.

According to some embodiments the apparatus also comprises a pulsed RF generator and pulsed RF power amplifier configured and operable to generate the excitation signals.

In some applications the magnetic field source unit comprises a thermostabilized permanent magnet assembly (e.g., made from rare-earth hard magnetic materials such as, but not limited to, $Sm_xCo_y$ and/or NdFeB alloys.) and/or a set of Helmholtz coils. For example, the Helmholtz coils may be configured and operable to correct temperature field drift and/or homogeneity.

In some embodiments the probehead further comprises a temperature sensor configured and operable to measure temperature of the tissue and generate temperature data indicative thereof, and the control unit is configured and operable to determine the at least one blood related parameter based on said temperature data.

According to another aspect, there is provided a method for use in non-invasive assessment of blood related parameters, the method comprising creating a substantially uniform magnetic field of about 0.15 to 0.5 Tesla within a magnetic field region at least partially overlapping with a test site where living tissue of an examined subject is to be located, to thereby magnetize blood in said living tissue, applying electromagnetic excitation signals of a range of 1 to 20 MHz in said test site to thereby affect the blood magnetization in the living tissue to cause nuclear spin echo signals from the living tissue, the electromagnetic excitation signals being applied with a predetermined time pattern, receiving, with a predetermined time pattern, electromagnetic radiation responsive to the nuclear spin echo signals from the living tissue, processing data corresponding to the received electromagnetic radiation, extracting therefrom data indicative of the nuclear spin echo signals from the living tissue, and determining relaxation time curves (e.g., using a multifunctional approximation) of blood constituents associated with the blood related parameters, to thereby determine at least one blood related parameter.

In some embodiments the determining of the blood related parameters comprises correlating the obtained relaxation time curves with a pre-determined matrix of relaxation time curves associated with the blood related parameters. In some applications the pre-determined matrix of relaxation times is calibrated to comply with a set of blood related parameters measured for the examined subject using conventional ex vivo blood test. In this way sensitivity of the blood assessment to a predetermined blood related parameter may substantially improved.

The excitation signals may comprise an overturning excitation signal having a predetermined time duration $\tau_i$ to overturn magnetization of blood constituents' nuclei towards a plane substantially perpendicular to direction of electromagnetic field of said signal, and a consecutive refocusing signal having a time duration $\tau_2 \geq \tau_1$ to turn magnetization of the blood constituents' nuclei towards a plane substantially perpendicular to the direction of electromagnetic field of said signal to form nuclear spin echo, said overturning and refocusing signals being separated by a predetermined time delay.

In some applications the excitation sequence comprises at least one additional excitation pulse applied before the overturning excitation signal and having a predetermined time duration $\tau_{pj}$ and predetermined time delay $\tau_{dk}$, to thereby form specific excitation sequence of electromagnetic field pulses suitable for exciting time dependent magnetizations of the blood constituents' nuclei.

Optionally, the time delay between the overturning and refocusing signals is adjusted to obtain the electromagnetic radiation responsive to the nuclear spin echo signals within a predefined time duration after the refocusing signal, said predefined time duration being greater than a predetermined dead time associated with the receiving of the electromagnetic radiation.

In some embodiments the method comprises applying the excitation signals a predetermined number of times, the time delay between the overturning signal and the refocusing signal being different in at least some of the excitation sequences, and determining the blood related parameters based on magnetization relaxation time curves determined for electromagnetic radiation received in response to the applied excitation signals.

In some applications the radio frequency of the excitation signals is set for carrying out NMR relaxometry for one or more of the following nuclei: $^1H$, $^{13}C$, $^{19}F$, and $^{31}P$.

The magnetization relaxation curve may be built from nuclear spin echoes obtained using the Hahn technique or solid echo technique. In possible applications, the electromagnetic excitation signals are carried out according to one or more of the following techniques: inversion recovery technique, progressive saturation technique, spin-lock technique, Hahn technique, and Carr-Purcell-Meiboom-Gill (CPMG) technique.

BRIEF DESCRIPTION OF THE DRAWINGS

In order to understand the invention and to see how it may be carried out in practice, embodiments will now be described, by way of non-limiting example only, with reference to the accompanying drawings, in which like reference numerals are used to indicate corresponding parts, and in which.

DETAILED DESCRIPTION OF EMBODIMENTS

Figure 1:
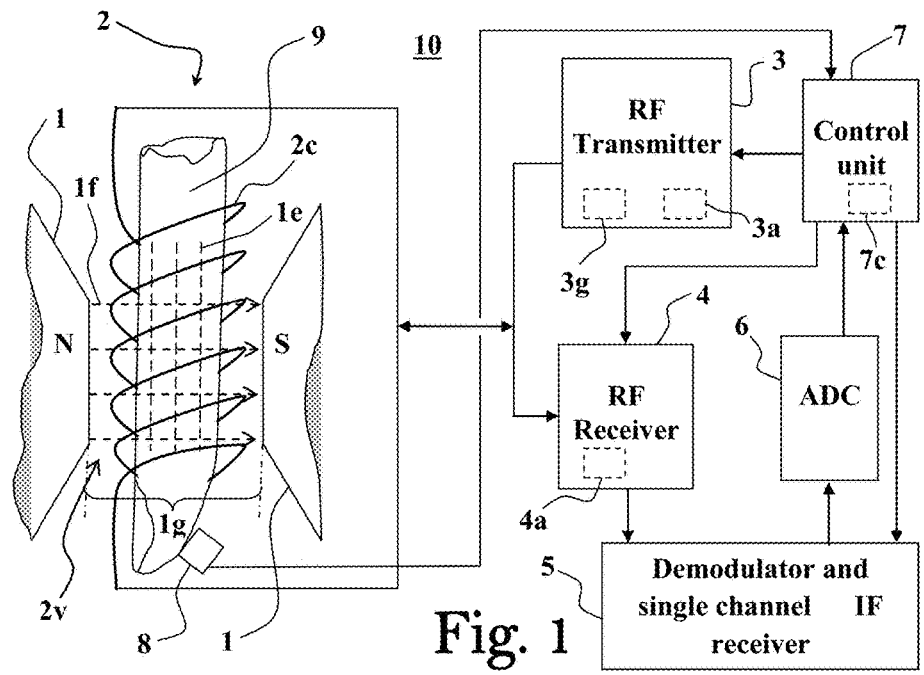
FIG. 1 is a block diagram of a non-invasive blood parameters measurement apparatus according to some possible embodiments.

The present invention is directed to techniques of in vivo non-invasive assessment of living blood parameters (such as glucose concentration, whole blood viscosity, haematocrit, oxygen saturation, pH) based on pulsed nuclear magnetic resonance (NMR) relaxometry applied to a finger of a subject.

According to some possible embodiments NMR signals are obtained from a finger phalange of an examined subject using a NMR probehead designed to accommodate at least a portion of the examined finger inside an inductive coil located between poles of a constant magnet assembly. Accordingly, the probehead may be configured to define an elongated test volume having geometrical dimensions suitable to accommodate the examined finger, and apply a magnetostatic field in a first direction inside the test volume. In this way, the magnetostatic field is applied over the examined finger once it is introduced into the test volume of the NMR probehead. The inductive coil of the probehead is preferably configured to apply electromagnetic excitation signals in a second direction being substantially perpendicular to the direction of the magnetostatic field applied by the constant magnet assembly, and acquire responsive electromagnetic relaxation signals from the examined organ.

In some possible embodiments the magnetostatic field applied by the constant magnet assembly is substantially perpendicular to a longitudinal axis of the examined finger i.e., perpendicular to the length of the examined finger. Accordingly, the electromagnetic excitation signals in such embodiments are applied in a direction being substantially perpendicular to the direction of the applied magnetostatic field such that it is substantially aligned with the longitudinal axis of the examined finger i.e., along the length of the examined finger.

The permanent magnet assembly may be adapted to apply a magnetostatic field having sufficient homogeneity (e.g., smaller than 10 ppm) over the test volume.

For example, in some embodiments an in vivo blood test is carried out by placing a finger phalange in the test volume of the probehead (i.e., where the magnetostatic field is generated), applying electromagnetic energy pulses (also referred to herein as excitation signals) by a coil of the probehead to excite nuclear spin echoes from protons (or other nuclei) in the living liquids, tissues and bones of the finger, and using the probehead coil to acquire electromagnetic relaxation signals from the finger phalange in response to the applied excitation signals. The acquired relaxation signals are then analyzed and processed to obtain NMR signals (e.g., spin-lattice and/or spin-spin relaxation signals) of the excited nuclei, and the blood parameters of the examined organ are determined based on the NMR signals obtained.

For instance, the nuclear spin-lattice and/or the spin-spin relaxation times of various kinds of protons (or other nuclei) in the fluids, tissues and bones, of the examined finger may be determined employing comprehensive multifunctional analysis of the nuclear spin echo decay measured after specific sequences of the excitation radio frequency pulses have been applied. In this way, assessment of various blood parameters may be carried out by correlating between a pre-determined matrix of various spin-lattice and spin-spin relaxation times/rates associated with blood parameters obtained from healthy subjects and nuclear spin-lattice and spin-spin relaxation times/rates obtained from the examined finger.

In some possible embodiments the magnetostatic field applied by the constant magnet assembly in the test volume is in the range of 0.15 to 0.5 Tesla, preferably about 0.3 Tesla. In some embodiments the frequency of the applied electromagnetic energy (also referred to herein as radio frequency pulses) is in the range of 1 MHz to 20 MHz, preferably about 10 to 20 MHz. For example, the frequency of the electromagnetic excitation signals applied by the probehead may be within a radio frequency band chosen to satisfy off-resonance excitation conditions e.g., by controllably shifting the frequency of the excitation signal pulses from the exact resonance frequency associated with nuclei of a particular material being examined.

In some possible embodiments, a pulsed radio frequency generator is used for generating the electromagnetic (radio frequency) excitation pulses applied over the examined finger through the inductive coil of the probehead.

With reference to FIG. 1, there is shown a compact (e.g., desktop size i.e., that may be placed on a desk, for example is size of a desktop printer) light weight (e.g., up to 5 kg) apparatus 10 for non-invasive in vivo assessment of blood parameters according to some possible embodiments. The apparatus 10 comprises an inductive NMR probehead 2 comprising an inductive coil 2c arranged along a test volume 2v defined inside the probehead 2. As shown in FIG. 1, the coil 2c is adapted to receive the finger 9 of the tested subject within its windings. The coil 2c may be made from wound electrical conducting wire made from silver, or silver plated copper, and having a wire cross sectional area of about 0.2 to 3 mm$^2$. For example, in some embodiments the internal diameter of the coil 2c should be sufficient to accommodate a phalange of a forefinger e.g., in the range of 20 to 35 mm, preferably about 30 mm. The number of coil turns in coil 2c may generally be about 20 to 50.

In the apparatus exemplified in FIG. 1 the finger 9 is introduced into the test volume 2v such that the magnetic field 1f from the magnet assembly 1 is applied over a portion of the finger 9 placed between the "N" and "S" poles of the magnet assembly 1. In this example, the permanent magnet assembly 1 is configured to apply a magnetostatic field 1f being substantially perpendicular to the length of the finger 9 and the coil 2c is adapted to apply the electromagnetic excitation signals 1e substantially along the length of the examined finger, such that the direction of the magnetic field 1f is substantially perpendicular to the direction of the excitation signals 1e.

For example, the permanent magnet assembly 1 may be constructed from two or more permanent magnets (e.g., made from samarium cobalt or neodinium-iron-boron alloys) arranged to define the test volume 2v between at least one pair of "N" and "P" poles of the permanent magnet arrangement. In some embodiments the volume in gap 1g, between the "N" and "P" poles of the magnet arrangement 1 defining the test volume 2v, is about 500 to 700 mm³ With this configuration the magnetic field 1f in the test volume 2v may generally be in the range of 0.15 to 0.5 Tesla.

In preferred embodiments the apparatus 10 is configured to apply a relatively low (e.g., 0.15 to 0.5 Tesla) and uniform constant magnetic field 1f over the examined finger, and off-resonance low radio frequency excitation signal pulses 1e (e.g., in the range of 1 MHz to 20 MHz) in a direction substantially perpendicular to the direction of the magnetic field 1f.

The magnet arrangement 1 may further include a pair of Helmholtz coils (not shown) configured and operable to correct temperature field drift and/or linear homogeneity of the constant magnetic field 1f generated by the permanent magnets. It is known that permanent magnets have significant temperature drift of their main field. This drift may be compensated by precise thermal stabilization of the magnet, or by applying correction current to the Helmholtz coils. The same coils may be used for improvement of the field's linear homogeneity.

It is however noted that other probehead arrangements may be employed to apply the magnetic field 1f and the excitation signals 1e in directions that are different from those demonstrated in FIG. 1, while guaranteeing that the direction of the magnetic field 1f is substantially perpendicular to the direction of the excitation signals 1e.

In some embodiments the probehead 2 further comprises circuitry for automatic switching between working resonant frequencies, and/or circuitry for automatic tuning and matching. The operation and design of such circuitries is known to those skilled in the art and thus will not be described herein for the sake of brevity.

It is noted that the magnetic field obtained using such small sized permanent magnet assembly 1 (e.g., about 80×60×40 mm³) cannot be homogeneous enough within the test volume 2v configured to accommodate a phalange of the finger 9. Therefore, the NMR tests carried out with apparatus 10 are performed using a magnetic field having quite modest (less than 20 ppm) homogeneity. This means that the NMR signals obtained using apparatus 10 have quite broad lines (in frequency domain) or short free induction decay (FID) (in time domain).

The registration of short FIDs is a complicated task (due to receiver dead time and circuit ringing artifacts), and therefore, according to some possible embodiments, measurements of the relaxation signals are carried out using nuclear spin echo signals in a time domain. In this way, the received NMR signals may be shifted from the "dangerous" dead time region of the circuitry. Moreover, the intensity of echoes in slightly inhomogeneous fields is typically quite strong, such that working with spin echo signals allow precise measurements of even short $T_1$ (i.e., spin-lattice relaxation times) and $T_2$ (i.e., spin-spin relaxation times) values (e.g., in the range of 20-100 microseconds).

The NMR apparatus 10 further comprises a pulsed RF transmitter 3 electrically connected to the probehead 2 and configured and operable to apply radio frequency excitation signals through the inductive coil 2c of the probehead. The probehead 2 is further connected to an RF receiver 4 configured and operable to receive through the coil 2c radio frequency electromagnetic relaxation signals from the examined finger 9 responsive to the radio frequency excitation signals applied by the RF transmitter 3. A single channel IF (intermediate frequency) receiver and demodulator unit 5 may be used to down convert the RF relaxation signals received from the receiver 4 and demodulate the down-converted signals. As exemplified in FIG. 1, the control unit 7 may be configured and operable to provide the demodulator unit 5 control signal for adjusting the gain of the IF receiver. For example, when operating with different materials (changing the nuclei under examination e.g., from $^1$H to $^{19}$F) unit 5 adjusts the frequency of signals generated by its local oscillator 5a, to obtain the same intermediate frequency (IF), and also adjusts the gain of the IF receiver.

In some embodiments the transmitter 3 comprises a pulsed RF generator 3g and pulsed RF power amplifier 3a configured and operable to generate high power RF excitation pulses to be applied to the examined finger 9 through the coil 2c of the probehead 2. In addition, in some possible embodiments the receiver 4 comprises a signal amplifier 4a configured and operable to amplify electromagnetic signals received from the coil 2c.

According to some possible embodiments, a pulse controller module 7c may be used in the control unit 7 to switch the apparatus operation 10 between its excitation and acquisition cycles. For example, the pulse controller module 7c may be configured to switch the generation of signals between frequencies usable for generation of excitation signals and frequencies usable for the demodulation carried out by the demodulator 5, to open pulse gate (not shown) and/or receiver protection gates (not shown), and suchlike.

It is worth noting that in the case of off-resonance detection, the signal received via the single channel IF receiver 5 cannot disappear altogether due to improper signal phase in this channel, whereas at on-resonance detection this may occur. The NMR signal detected by the single channel IF receiver and demodulator unit 5 is digitized by the analog to digital converter (ADC) 6, and the digitized NMR signal from the ADC 6 is then received and processed by the control unit 7 to determine one or more blood parameters therefrom.

In some possible embodiments the probehead 2 further comprises a temperature sensor 8 configured and operable to measure the temperature of the examined finger 9, and generate data indicative thereof. The measurement data generated by the temperature sensor 8 is received and processed by the control unit 7, and used thereafter to adjust reference data used in the determination of the blood related parameters. Since most nuclear relaxation rates in liquids are highly sensitive to temperature, it is very important to measure the temperature of examined organ and adjust the reference data used in the blood related parameters determination stage accordingly. Thus, in some embodiments employing a correlation matrix to determine the blood related parameters, the measured temperature of the examined finger is one of the main parameters in the database of reference data used for the constructions of the correlation matrix, e.g., the relaxation time $T_1$ corresponding to the blood viscosity at some fixed temperature, or a relaxation curve obtained for glucose at a certain temperature, and suchlike.

In operation, a sequence of at least two relatively short (hard, e.g., having 0.5 to 3 gsec pulse lengths) π/2 and π phase shifted (e.g., π/2 phase shifted inversion pulse followed by π phase shifted refocusing pulse) RF pulses at off-resonance low frequency are applied to the examined finger 9 (or any other designated body part) inserted into the NMR probehead 2. Short hard (also known as non-selective) off-resonance pulses provide enhanced nuclear spin echo signals from all corresponding nuclei of the examined finger 9 (or other body portion) including not only nuclei of the living liquids characterized by narrow NMR lines, but also of nuclei in semi-immobilized and immobilized tissues and bones characterized by broad NMR lines, and consequently, shorter relaxation times. The same excitation technique allows registration of NMR signals from nuclei located in areas where the polarizing magnetic field of the permanent magnet is inhomogeneous. Compared with the continuous wave (CW) method disclosed in U.S. Pat. No. 7,635,331, the technique disclosed herein increases total nuclear magnetization observed and makes the blood parameters measurement apparatus 10 more sensitive and reliable.

The advantages of using low field/low frequency NMR apparatus originate from two principal practical aspects. First, relatively small weight and low-cost permanent magnets of up to 0.5 Tesla are commercially available nowadays (e.g., PM 1055 from Metrolab, Switzerland or magnets of S-25-S-30 series from Supermagnete, Switzerland). Second, at low RF frequencies (e.g., 1-20 MHz) characteristic relaxation times of the most abandoned blood nuclei—protons drop from seconds to fraction of seconds (R. A. Brooks, J. H. Battocletti, A. Sanges Jr., S. J. Larson, R. L. Bowman and V. Kudravcev, Nuclear Magnetic Relaxation in Blood, IEEE Transactions on Biomedical Engineering, V. 22(1) 1975, p. 12), that allows shortening the total examination time from tens of minutes to a few minutes. Hard off-resonance pulse excitation and detection of the nuclear spin echo signals allows also using a single-channel data acquisition that makes the tester simpler and allows reducing its final cost.

Multifunctional analysis of nuclear magnetization decays, such as "longitudinal" spin-lattice relaxation times $T_{1i}$ (where i is a positive integer used for indexing spin-lattice relaxation times associated with different materials), "longitudinal" spin-lattice relaxation time in rotating frame $T_{1\rho i}$ and "transverse" spin-spin relaxation time $T_{2i}$), for each i-constituent of N distinguishable blood constituents, allows more precise selective determination of the living blood parameters (e.g., blood glucose level, blood viscosity, haematocrit, oxygen saturation, pH, and suchlike) by correlating between a pre-determined matrix of relaxation times/rates associated with various blood parameters measured in healthy subjects and the nuclear spin-lattice relaxation times obtained from the finger of the examined subject.

The proposed NMR apparatus 10 allows individual calibration of the pre-determined matrix of various blood parameters to a set of blood parameters measured for the same individual by conventional invasive blood tests aiming to improve sensitivity of the blood assessment to the most critical (for this individual) blood parameters. This calibration assumes exchanging relaxation times and blood parameters from the pre-determined (by clinical trials) correlation matrix by real relaxation times/rates and blood parameters obtained by precise measurements done on the individual. Thus, for individuals suffering from diabetes, for example, the general pre-determined correlation matrix may be adjusted according to personal blood glucose levels of the specific individual as obtained using conventional invasive blood tests, whereas for individuals suffering from hyperviscosity syndrome the adjustment of the correlation matrix may take into account personal variations of the blood viscosity obtained through use of conventional invasive blood tests.

Figure 8:
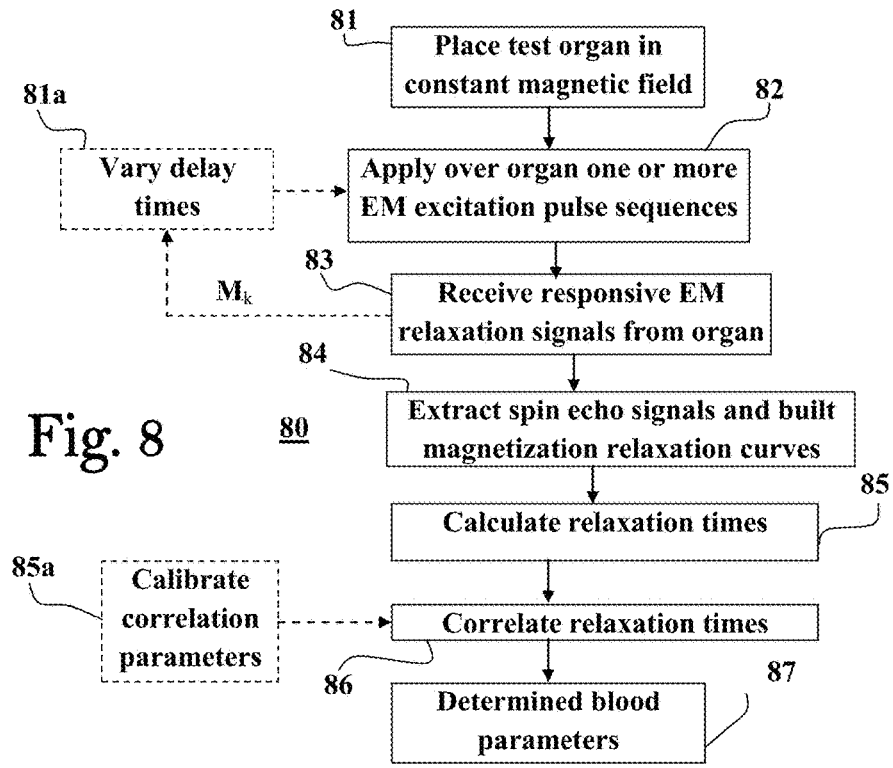
FIG. 8 is a flowchart demonstrating a process for assessing blood parameters of a subject according to some possible embodiments.

FIG. 8 is a flowchart demonstrating a process 80 for assessing blood parameters of a subject according to some possible embodiments. The process 80 commences in step 81 by introducing the test organ (e.g., finger phalange) into a test volume (2v) in which the organ is under constant magnetic field (1f) conditions. Next, in step 82, one or more electromagnetic (EM) excitation pulse sequences are applied over the test organ, in step 83 responsive relaxation signals are received from the test organ, and in step 84 magnetization relaxation curves are constructed from the received spin echo signals. Optionally, in step 81a, one or more delay times between successive excitation pulse signals in each excitation pulse sequence are adjusted before they are applied to the test organ in step 82. The applying of excitation signals and acquiring responsive relaxation signals of steps 81 and 82, and optional step 81a of adjusting the delay times, may be repeated a plurality ($M_k$) of times to improve the overall signal to noise ratio and improve the detection of spin echo signals in step 84.

In step 85 nuclear relaxation times are determined from the magnetization relaxation curves for one or more blood constituents. The relaxation times obtained are then correlated in step 86 with respective relaxation times associated with blood parameters collected from multiple subjects, both healthy and deceased. The correlation results are then used in step 87 to determine blood parameters of the examined subject. Optionally, a calibration step 85a may be performed before carrying out the correlation step 86. The calibration step 85a allows adjusting the process for the assessment of blood parameter of a specific subject, for example, by adjusting the one or more relaxation times to comply with blood parameters of the examined subject preliminarily obtained through the invasive blood taking procedure.

EXAMPLES

Example 1

The first phalange of a forefinger of a living subject was placed in a specially designed NMR probe comprising a copper coil (2c) having an internal diameter of about 15 mm and length of about 20 mm. The copper coil in this example is part of a tuned tank circuit (i.e., resonant circuit e.g., LC circuit), placed between the poles of an electromagnet of a commercial Varian E-12 EPR spectrometer. In vivo measurements were carried out in a fixed magnetic field $B_0$=0.273 Tesla at radiofrequency $f_0$=11.62 MHz. The thermal stabilization of the examined finger was kept by internal body temperature at normal physiological conditions (36.6±0.5° C.). Measurements of spin-spin relaxation times $T_{2i}$ (where i is a positive integer used for the indexing of excitation/SE acquisition cycles) of $^1$H nuclei in the examined forefinger phalange were conducted using a single RF channel of a commercial Tecmag Libra-NMRkitII pulsed solid state NMR spectrometer by applying off-resonance ($\Delta f$=5 kHz) excitation in the form of phase cycled Hahn spin-echo sequence with a variable delay $\tau_{SEi}$ defining a time duration between the end of the excitation pulses (21 and 22 in FIG. 2) and a peak (23p) of their respective relaxation signals (23). The homogeneity of the EPR spectrometer's magnet is modest enough to provide quite short $T_2^*$ values that allow observation of strong Hahn spin echo (SE) signals.

Figure 2:
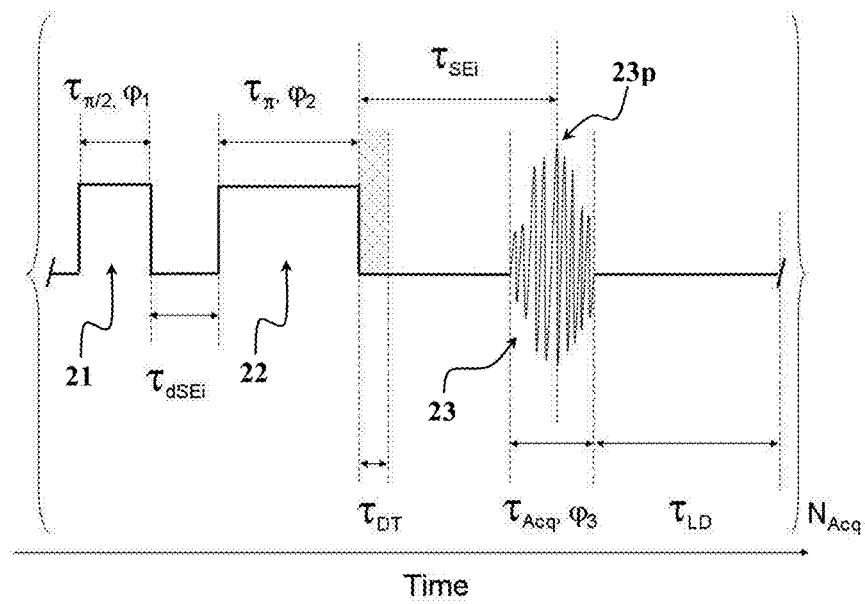
FIG. 2 schematically illustrate a possible Hahn spin echo excitation pulse sequence, and acquisition having a variable delay usable for measurements of $T_{2i}$ spin-spin relaxation times in living blood according to some possible embodiments.

FIG. 2 graphically illustrates the excitation sequence used in this example. As seen in FIG. 2 the first electromagnetic exciting pulse 21 ($\pi/2$ phase shifted) having $\tau_{\pi/2}$ duration and phase $\varphi_1$ is separated from the second (refocusing) electromagnetic exciting pulse 22 ($\pi$ phase shifted) having $\tau_\pi$ duration and phase $\varphi_2$ by a variable delay $\tau_{dSEi}$. SE signal acquisition with the received phase $\varphi_3$ starts after a time duration $\tau_{SEi}$−$\tau_{Acq}$/2 has passed since the end of the second electromagnetic exciting pulse 22, where $\tau_{SEi}$=($\tau_{\pi/2}$+$\tau_\pi$)/2+$\tau_{dSEi}$. The time delays $\tau_{dSEi}$ between each pair of consecutive excitation RF pulses 21 and 22 are chosen such that $\tau_{SEi} > \tau_{DT}$, where $\tau_{DT}$ is the receiver dead time. Upon completion of the acquisition of the relaxation signals, the system is changed into a wait state during the recycle delay time $\tau_{LD} \sim 1.3\, T_1$ ($T_1$ being the spin-lattice relaxation time for $^1H$), during which no excitation pulses are applied before the next excitation/SE acquisition cycle. While consecutive excitation/SE acquisition cycles have the same delay $\tau_{dSEi}$ times between their respective excitation RF pulses 21 and 22, their phases $\varphi_1$, $\varphi_2$ and $\varphi_3$, are different, as chosen according to the phase cycling scheme being used (e.g., two, four or sixteen phases). The use of some phase cycling techniques effectively quenches all powerful RF pulse passage artifacts (like tank circuit ringing etc.), which allows precise measurements of the SE signals at long delays $\tau_{dSEi}$.

Figure 3:
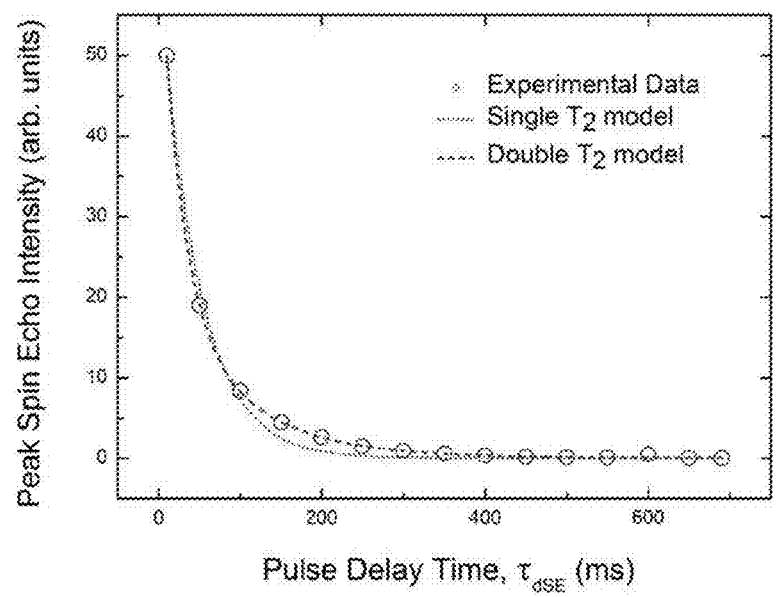
FIG. 3 shows graphical plots of experimental spin echo values, best least-square fit carried out using a single exponential model, and best least-square fit carried out using a double exponential model, obtained with the setup used in Example 1.

In order to improve the SE signal to noise ratio at each delay $\tau_{dSEi}$ the pulse excitation/SE acquisition cycle is repeated $N_{Acq}$ times where, according to the corresponding phase cycle scheme, $N_{Acq}$ is a number divisible by two, four or sixteen. The peak values of the SE magnitude, obtained by the digital quadrature detection technique, as a function of the delay $\tau_{dSE}$ between the $\pi/2$ and it pulses are plotted in FIG. 3. FIG. 3 shows a typical $^1H$ nuclei spin echo decay curve obtained on the forefinger phalange by NMR at $f_0 = 11.62$ MHz. The open circles in FIG. 3 represent experimental spin echo values, the dashed line curve in FIG. 3 is a plot of best least-square fit carried out using a single exponential model, and the dotted line is a plot of best least-square fit carried out using a double exponential model.

The best least-square fitting supposing the model of only one type of $^1H$ nuclei $SE = SE_0 \cdot e^{-2\tau_{dSE}/T_2}$ provides $T_2 = 94 \pm 4$ ms and $R^2 = 0.9933$, whereas the best least-square fitting supposing the model of two types of $^1H$ nuclei $SE = SE_{01} \cdot e^{-2\tau_{dSE}/T_{12}} + SE_{02} \cdot e^{-2\tau_{dSE}/T_{22}}$ provides $T_{21} = 196 \pm 9$ ms, $T_{22} = 52 \pm 2$ ms, $R^2 = 0.9999$, and the weighting ratio between two types of nuclei is $SE_{01}/SE_{02} = 20:46$. This example clearly demonstrates that the relaxation measurements of the $^1H$ nuclei in the living forefinger phalange reveals at least double component structure of this $^1H$ nuclear system.

Example 2

In vivo $^1H$ spin-lattice relaxation times measurements were done on a living forefinger phalange of an individual using the instrumental setup used in Example 1 ($f_0 = 11.62$ MHz). The thermal stabilization of the examined finger was kept by internal body temperature at normal physiological conditions (36.6±0.5° C.). Off-resonance ($\Delta f = 5$ kHz) excitation of $^1H$ nuclei and SE acquisition was carried out using the saturation comb excitation sequence combined with phase cycled spin echo detection, as demonstrated in FIG. 4.

This excitation sequence allows shortening of the test time duration needed for precise measurements of long spin-lattice relaxation times $T_1$. The excitation sequence exemplified in FIG. 4 begins with of a train (comb) of m (m=8÷20) saturating ($\pi/2$ phase shifted) pulses 41, each having $\tau_{\pi/2}$ time duration and phase $\varphi_1$, and separated by delay times $\tau_{Sat}$, where $T_2^* < \tau_{Sat} < T_1$. Following the m saturating pulse train (comb) of m (m=8÷20) saturating pulses 41 there is a variable delay time $\tau_{dRi}$. Thereafter the excitation sequence proceeds with the reading ($\pi/2$ phase shifted) pulse 42 having a $\tau_{\pi/2}$ time duration and phase $\varphi_1$, followed by a fixed delay having a $\tau_{dSE}$ time duration, and the (i$^{th}$) excitation sequence is then concluded with the refocusing ($\pi$ phase shifted) pulse 43 having a $\tau_{\pi}$, time duration and phase $\varphi_2$. The acquisition of the SE signal is then performed with the receiver phase $\varphi_3$ starting at a $\tau_{SE} - \tau_{Acq}/2$ time duration after the end of the refocusing pulse 43, where $\tau_{SE} = (\tau_{\pi/2} + \tau_{\pi})/2 + \tau_{dSE}$. The time delay $\tau_{dSE}$ between the reading pulse 42 and the refocusing pulse 43 is chosen such that $\tau_{SE} > \tau_{DT}$, where $\tau_{DT}$ is the receiver dead time. Upon completion of the acquisition event, the system enters a wait state having a time duration $\tau_{LD} \ll T_1$, during which no excitation pulses are applied. After the time duration $\tau_{LD}$ a new (i+1) excitation/SE acquisition cycle is commenced. While the same delay time $\tau_{dRi}$ is used in consecutive excitation/SE acquisition cycles, a set of different phases $\varphi_1$, $\varphi_2$ and $\varphi_3$ are chosen according to a predetermined phase cycling scheme that is being used (e.g., two, four or sixteen phases). The use of some phase cycling techniques effectively quenches all powerful RF pulse passage artifacts (like tank circuit ringing etc.), which allows precise measurements of the weak SE signals at short delays $\tau_{dRi}$.

In order to improve the SE signal to noise ratio at each delay $\tau_{dRi}$ the saturation comb excitation/SE acquisition cycle is repeated $N_{Acq}$ times, where, according to the corresponding phase cycle scheme being used, $N_{Acq}$ is a number divisible by two, four or sixteen. The peak values (44p) of the SE magnitude (magnetization M) obtained by the digital quadrature detection technique, as a function of the delay $\tau_{dRi}$ between the saturating pulses (41) train (comb) and reading pulse 42 are plotted in FIG. 5.

Figure 5:
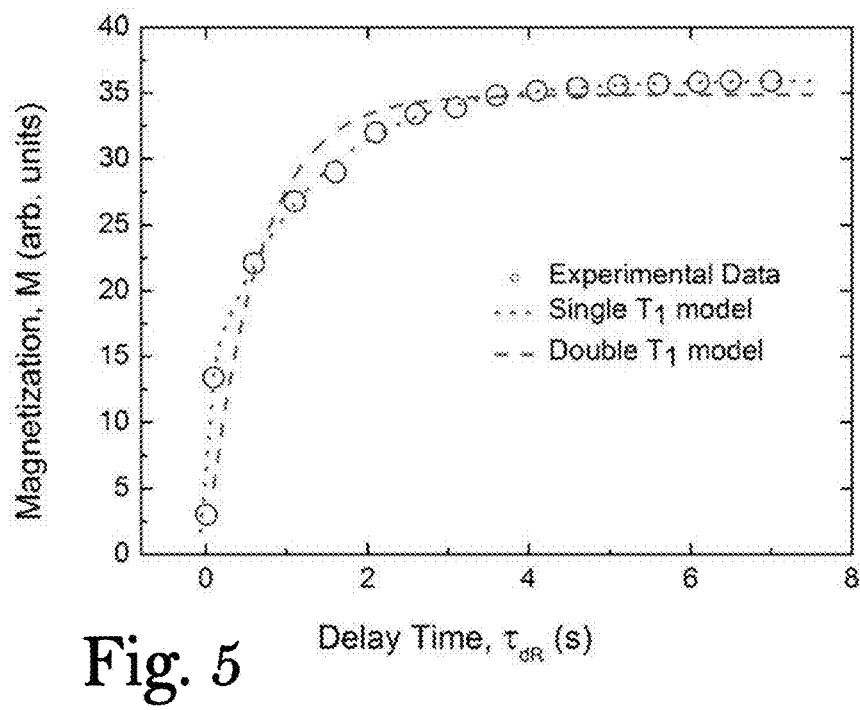
FIG. 5 shows graphical plots of experimental spin echo values, best least-square fit carried out using a single exponential model, and best least-square fit carried out using a double exponential model, obtained with the setup used in Example 2.

FIG. 5 shows graphical plots of a typical $^1H$ nuclei magnetization curve obtained from the forefinger phalange by NMR excitation at $f_0 = 11.62$ MHz. The open circles in FIG. 5 represent experimental magnetization values, the dashed line is a plot of best least-square fit carried out using a single exponential model, and the dotted line is a plot of best least-square fit carried out using a double exponential model.

Best least-square fit supposing the model of only one type of $^1H$ nuclei $M = M_0 \cdot (1 - e^{-\tau_{dR}/T_1})$ provides $T_1 = 636 \pm 98$ ms and $R^2 = 0.9281$, whereas best least-square fit supposing the model of two types of $^1H$ nuclei $M = M_{01} \cdot (1 - e^{-\tau_{dR}/T_{11}}) + M_{02} \cdot (1 - e^{-\tau_{dR}/T_{12}})$ provides $T_{11} = 1250 \pm 43$ ms, $T_{12} = 46 \pm 5$ ms, $R^2 = 0.9994$, and the weighting ratio between the two types of nuclei is $M_{01}/M_{02} = 22:13$. This example clearly demonstrates that the relaxation measurements of the $^1H$ nuclei in the living forefinger phalange reveals at least double component structure of this $^1H$ nuclear system.

Example 3

Figure 4:
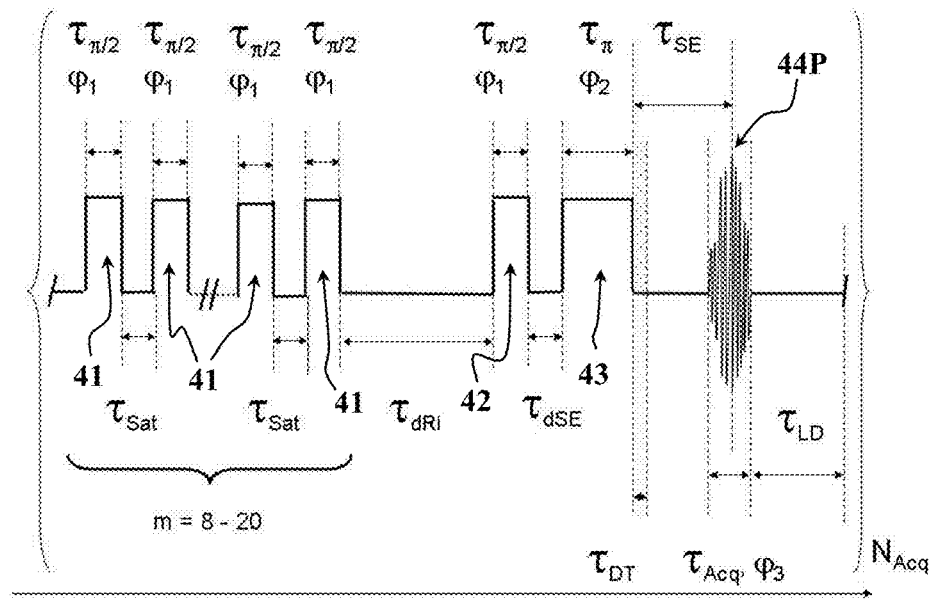
FIG. 4 schematically illustrates a saturation comb excitation sequence combined with phase cycled Hahn spin echo detection, and having a variable delay time $\tau_{dRi}$, as used in Example 2 to measure $T_{1i}$ spin-lattice relaxation times in living blood.

$^1H$ spin-lattice relaxation times measurements were carried out in vivo on a series of living forefinger phalanges of individuals having different blood glucose levels using the instrumental setup used in Example 1 ($f_o = 11.62$ MHz) and saturation comb sequence combined with phase cycled spin-echo detection as used in Example 2 (see FIG. 4). Thermal stabilization of the examined finger phalanges was maintained by internal body temperature at normal physiological conditions (36.6±0.5° C.). All individuals under the tests did not suffer from diseases affecting blood viscosity (like polycythemia, hydraemia etc.). Parallel assessment of the blood glucose level was done using a commercial Abbot FreeStyle Lite invasive strip-type glucose meter. Results of the series of tests are shown in FIG. 6, showing dependence of the $^1H$ spin-lattice relaxation time $T_{11}$ measured on the series of forefinger phalanges as a function of the blood glucose content.

Figure 6:
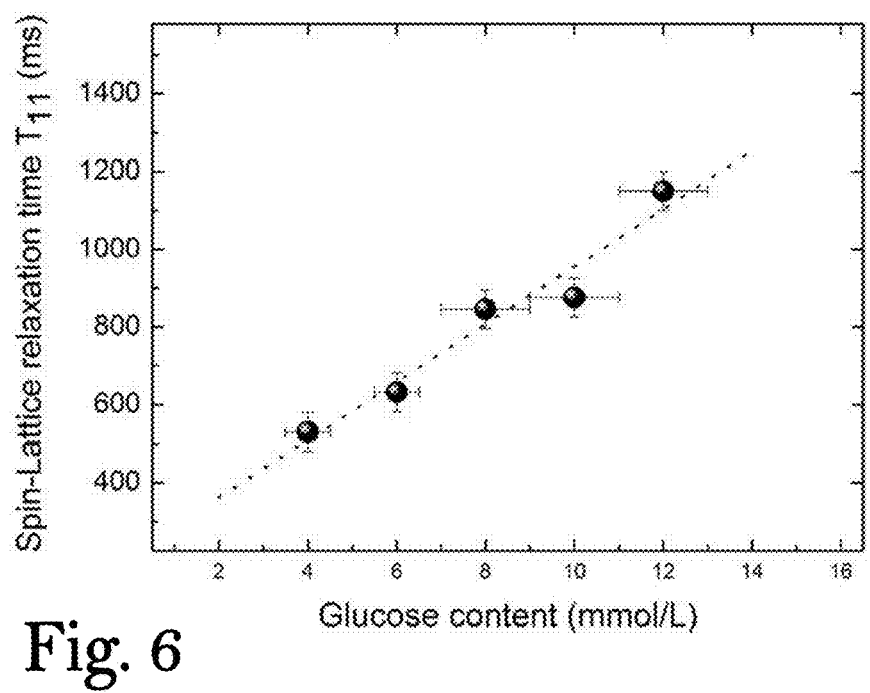
FIG. 6 is a graphical illustration showing the dependence of the $^1$H spin-lattice relaxation time $T_{11}$ measured in Example 3 on a series of forefinger phalanges as a function of blood glucose content.

FIG. 6 demonstrates clear dependence of the $^1H$ spin-lattice relaxation time $T_{11}$ on the blood glucose content. Within the normal physiological range of blood glucose levels, and above the normal level the relaxation time $T_{11}$ shows a tendency to increase.

Example 4

$^1$H spin-lattice relaxation times measurements were carried out ex vivo on a series of fresh blood samples collected from individuals having different blood viscosity parameters. The collected time samples were placed inside NMR tubes having a 5 mm external diameter and a 20 mm length, and entered into the NMR probe coil, using the instrumental setup used in Example 1 ($f_0$=11.62 MHz) and saturation comb sequence combined with phase cycled spin-echo detection as used in Example 2 (see FIG. 4). For these samples the best least square fit was obtained by using a single spin-lattice relaxation time $T_1$. The thermal stabilization of the samples under the tests was carried out at the temperature 36.6±0.5° C. by external nitrogen flow temperature accessories. All individuals under these tests had approximately the same blood glucose content (within the range of 6-8 mmol/L estimated by a commercial invasive strip-type glucometer). Parallel assessment of the fresh blood viscosity was carried out using a commercial Brookfield rotational viscometer.

Figure 7:
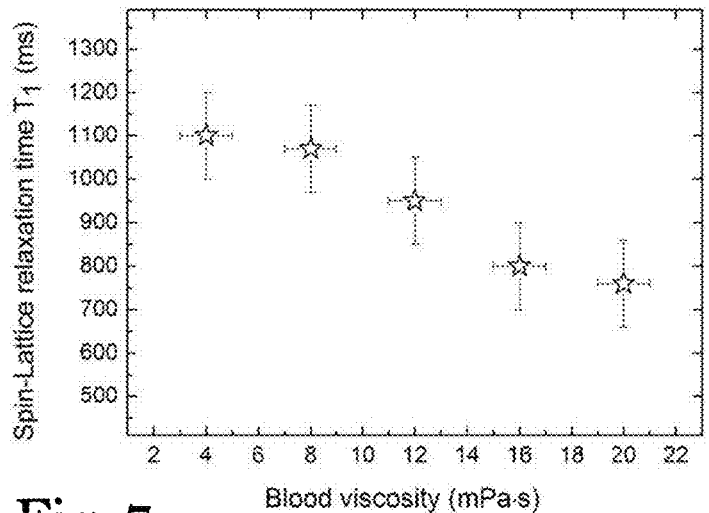
FIG. 7 is a graphical illustration showing dependence of the $^1$H spin-lattice relaxation time $T_1$ measured in Example 4 on a series of fresh blood samples as a function of blood viscosity.

Results of the series of tests are shown in FIG. 7. The results shown in FIG. 7 demonstrate clear dependence of the $^1$H spin-lattice relaxation time $T_1$ on the blood viscosity. Notably, deviations of the blood viscosity from its normal physiological range (4-5 mPa·s) at constant blood glucose level cause measurable shortening of the relaxation time $T_1$.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A method for use in assessment of blood related parameters, wherein the method provides non-invasive in vivo assessment of blood parameters of an examined subject, the method comprising:

creating a static magnetic field in a range of 0.15 to 0.5 Tesla within a magnetic field region at least partially overlapping with a test site where a body part of said examined subject is located, to thereby magnetize blood in living tissue of said body part;

providing time patterns predetermined on the basis of characteristic nuclear magnetization curves associated with blood constituents and using said time patterns for applying hard off-resonance electromagnetic excitation signals of a range of 1 to 20 MHz in said test site to thereby affect the blood magnetization in the living tissue to cause nuclear spin echo signals from the living tissue, and for receiving respective off-resonance excited electromagnetic radiation response due to the nuclear spin echo signals from the living tissue acquired as sets of one-dimensional spin echo signals obtained with at least one variable delay time between the sets of one-dimensional spin echo signals;

using a single channel RF receiver unit to down convert the received off-resonance excited electromagnetic response in analog domain, and generate therefrom a set of measured multi-dimensional data indicative of the nuclear spin echo signals; and processing said set of measured multi-dimensional data and extracting therefrom data indicative of nuclear magnetization curves associated with the nuclear spin echo signals from the living tissue, determining by multifunctional analysis of said nuclear magnetization curves nuclear spin relaxation times or rates of the blood constituents, and using said nuclear spin relaxation times or rates to determine at least one blood related parameter associated with said blood constituents.

2. The method according to claim 1 wherein the determining of the blood related parameters comprises correlating the nuclear spin relaxation times or rates of the blood constituents with a pre-determined matrix of relaxation times or rates associated with the blood related parameters.

3. The method according to claim 2 comprising calibrating the pre-determined matrix of relaxation times to comply with a set of blood related parameters measured for the examined subject using a conventional ex vivo blood test.

4. The method according to claim 3 wherein the calibrating is carried out before the correlating of the nuclear spin relaxation times or rates of the blood constituents to thereby improve sensitivity of the blood assessment to a predetermined blood related parameter.

5. The method according to claim 1 wherein the blood related parameters comprise one or more of the following: blood glucose content, blood viscosity, blood haematocrit, blood oxygen saturation, and blood pH.

6. The method according to claim 1 wherein the applying of the hard off-resonance electromagnetic excitation signals comprises controllably shifting the frequency of the hard off-resonance electromagnetic excitation signals from a resonance frequency associated with nuclei of a particular material being examined.

7. The method according to claim 1 wherein the hard off-resonance electromagnetic excitation signals comprise a set of excitation pulse sequences, each sequence comprising an overturning excitation signal having a predetermined time duration $t_1$ and configured to overturn magnetization of blood constituents' nuclei towards a plane perpendicular to direction of electromagnetic field of said signal, and a consecutive refocusing pulse signal having a time duration $t_2 \geq t_1$ and configured to turn magnetization of the blood constituents' nuclei towards a plane perpendicular to the direction of electromagnetic field of said signal to form nuclear spin echo, said overturning and refocusing signals being separated by a predetermined time delays $t_{dSEi}$, the method comprising cycling phases of the excitation pulses for allowing precise measurements with said time delays $t_{dSEi}$.

8. The method according to claim 7 wherein the excitation sequence comprises at least one additional excitation pulse applied before the overturning excitation pulse signal, to thereby form specific excitation sequence of electromagnetic field pulses suitable for exciting time dependent magnetizations of the blood constituents' nuclei.

9. The method according to claim 7 wherein the time delays between the overturning and refocusing excitation pulse signals is adjusted to obtain the off-resonance excited electromagnetic radiation response due to the nuclear spin echo signals within a predefined time duration after the refocusing signal, said predefined time duration being greater than a predetermined dead time associated with the receiving of the electromagnetic radiation.

10. The method according to claim 7 comprising:

applying the hard off-resonance electromagnetic excitation signals a predetermined number of times, the time delay between the overturning signal and the refocusing signal being different in at least some of the excitation sequences; and determining the blood related parameters based on multiple non single exponential magnetization relaxation curves determined for electromagnetic radiation received in response to the applied excitation signals.

11. The method according to claim 1 wherein the radio frequency of the hard off-resonance electromagnetic excitation signals is set for carrying out NMR relaxometry for one or more of the following nuclei: $^1H$, $^{13}C$, $^{19}F$, and $^{31}P$.

12. The method according to claim 1 wherein the magnetization relaxation curves are built from nuclear spin echoes obtained using the Hahn technique or solid echo technique.

13. The method according to claim 1 wherein applying of the hard off-resonance electromagnetic excitation signals being carried out according to one or more of the following techniques: inversion recovery technique, progressive saturation technique, spin-lock technique, Hahn technique, and Carr-Purcell-Meiboom-Gill (CPMG) technique.

14. The method according to claim 1 wherein the determined magnetization relaxation curves comprise: $T_{1i}$ spin-lattice magnetization relaxation curves, $T_{1\rho i}$ spin-lattice magnetization relaxation in rotating frame curves, and $T_{2i}$ spin-spin magnetization relaxation curves.

* * * * *